United States Patent

Hayakawa et al.

Patent Number: 5,126,499
Date of Patent: Jun. 30, 1992

[54] PROCESS FOR THE PRODUCTION OF HYDROCARBONS WITH TWO OR MORE CARBON ATOMS FROM METHANE

[75] Inventors: Takashi Hayakawa; Katsuomi Takehira; Hideo Orita; Masao Shimizu, all of Tsukuba; Yoshihito Watanabe, Takasuki, all of Japan

[73] Assignee: Director-General of Agency of Industrial Science and Technology, Japan

[21] Appl. No.: 672,487

[22] Filed: Mar. 20, 1991

[30] Foreign Application Priority Data

Mar. 31, 1990 [JP] Japan .................................. 2-87257

[51] Int. Cl.$^5$ .............................................. C07C 2/00
[52] U.S. Cl. ..................... 585/500; 585/654; 585/656; 585/658; 585/700; 585/943
[58] Field of Search ............... 585/500, 654, 656, 658, 585/700, 943

[56] References Cited

U.S. PATENT DOCUMENTS

| | | | |
|---|---|---|---|
| 4,239,658 | 12/1980 | Mitchell, III et al. | 585/943 |
| 4,654,459 | 3/1987 | Sofranko | 585/500 |
| 4,721,828 | 1/1988 | Withers | 585/943 |
| 4,795,842 | 1/1989 | Gaffney et al. | 585/700 |
| 4,857,497 | 8/1989 | DeJong et al. | 585/700 |
| 4,982,041 | 1/1991 | Campbell | 585/943 |

FOREIGN PATENT DOCUMENTS 0205117 6/1986 European Pat. Off. .
2192894A 1/1988 United Kingdom .

OTHER PUBLICATIONS

Chemical Abstracts, vol. 109, No. 4, Jul. 25, 1988, p. 122, 25112v.
Chemical Abstracts, vol. 108, No. 12, Mar. 24, 1988, p. 385, 100466y.

Primary Examiner—Patrick P. Garvin
Assistant Examiner—E. D. Irzinski
Attorney, Agent, or Firm—Lorusso & Loud

[57] ABSTRACT

A process for the production of hydrocarbons having 2 or more carbon atoms by oxidative coupling of methane includes a step of contacting a feed gas containing methane with an oxide of metals having the following composition:

$$MCo_{1-x}Fe_xO_y.$$

wherein M stands for at least one alkaline earth metal x is a number greater than 0 but not greater than 1 and y is a number in the range of 2.5–3.5, at a temperature of 500°–1000° C.

4 Claims, No Drawings

PROCESS FOR THE PRODUCTION OF HYDROCARBONS WITH TWO OR MORE CARBON ATOMS FROM METHANE

BACKGROUND OF THE INVENTION

This invention relates to a process for the production of hydrocarbons having two or more carbon atoms by the oxidative coupling of methane.

While methane is abundantly obtained from natural gas, its utility is now limited only to a few applications. Because of possible exhaustion of petroleum in the not very distant future, the use of methane as a raw material for chemical products is highly desired.

A method is known to obtain $C_2$ or higher hydrocarbons such as ethane and ethylene by contacting a mixed gas containing methane and oxygen with a catalyst such as lithium-magnesium oxide (J. Am. Chem. Soc., 1985, 5062 (1985)), a rare earth metal oxide (Japanese Tokyo Kokai 61-165340), a rare earth metal carbonate (Japanese Tokyo Kokai 1-143838), an alkaline earth metal oxide (Chem. Lett., 1985, 49 (1985)) and perovskite compounds, e.g. A103 (J. Am. Chem. Soc., Chem. Commun. 49, (1986)), $BaCeO_3$ (Chem. Lett., 1987, 1985) and $BaPb_{1-x}BiO_3$ (J. Mater. Science Lett., 8, 17 (1989). Because the known method is carried out in the presence of molecular oxygen, by-products such as carbon monoxide or carbon dioxide are apt to be yielded so that the selectivity to $C_2$ or higher hydrocarbons is lowered. Further, even if the production of such by-products can be suppressed and the $C_2$ or higher hydrocarbons can be produced with both high yield and selectivity, it is necessary to concentrate the $C_2$ or higher hydrocarbon product because the concentration of methane in the feed gas is not high.

SUMMARY OF THE INVENTION

It is, therefore, an object of the present invention to provide a process which can yield $C_2$ or higher hydrocarbons with a high selectivity by oxidative coupling of methane.

Another object of the present invention is to provide a process of the above-mentioned type in which the concentration of $C_2$ or higher hydrocarbons in the product gas is high.

It is a further object of the present invention to provide a process of the above-mentioned type which does not use molecular oxygen in the oxidative coupling stage.

In accomplishing the foregoing, there is provided in accordance with one aspect of the present invention a process for the production of hydrocarbons having 2 or more carbon atoms, comprising contacting a feed gas containing methane with an oxide of metals having the following composition:

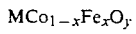

$$MCo_{1-x}Fe_xO_y$$

wherein M stands for at least one alkaline earth metal x is a number greater than 0 but not greater than 1 and y is a number in the range of 2.5–3.5, at a temperature of 500–1000° C.

In another aspect, the present invention provides a process for the production of hydrocarbons having 2 or more carbon atoms, comprising the steps of:

(a) introducing a feed gas containing methane into a reaction zone and contacting same with an oxide of metals contained in said reaction zone at a first temperature in the range of 500–1000° C., said oxide of metals having the following composition:

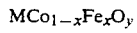

$$MCo_{1-x}Fe_xO_y$$

wherein M stands for at least one alkaline earth metal x is a number greater than 0 but not greater than 1 and y is a number in the range of 2.5–3.5; and (b) introducing a regeneration gas containing molecular oxygen into said reaction zone and contacting same with said oxide of metals at a second temperature which is not lower than said first temperature, wherein steps (a) and (b) are alternately repeated.

The present invention does not use molecular oxygen for the oxidative coupling of methane. Rather, the oxide of metals of the above formula serves both as a carrier of oxygen required for effecting the coupling and as a catalyst therefore.

Other object, features and advantages of the present invention will become apparent from the detailed description of the invention to follow.

DETAILED DESCRIPTION OF THE INVENTION

The oxide of metals to be used as an oxygen carrier and/or catalyst in the present invention has the following composition:

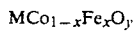

$$MCo_{1-x}Fe_xO_y$$

wherein M stands for at least one alkaline earth metal x is a number greater than 0 but not greater than 1 and y is a number in the range of 2.5–3.5. The alkaline earth metal M is preferably magnesium, calcium, strontium or barium, more preferably strontium or barium. The number x is preferably 0.1–0.6 and the number y is preferably 2.7–3.1. The use of metal oxides of the above composition having a crystallographical phase of a perovskite structure is particularly preferred.

The metal oxides may be produced by the following method. Aqueous solutions of salts (such as nitrates) of at least one alkaline earth metal, cobalt and iron are mixed in proportions corresponding to the desired composition of the metal oxides to be prepared. To this mixture are then added at least equimolar amounts of a ligand agent such as citric acid and a suitable amount of a dispersing agent such as ethylene glycol. The resulting mixture is heated in a rotary evaporator at about 100° C. until the generation of nitrogen oxide gas is no longer detected. The resultant sol is dried at 170–200° C. and further heated in air at 220–250° C. to remove organic matters remaining therein. This is then calcined at 800–900° C. The calcined metal oxides product generally shows an X-ray diffraction pattern typical to perovskite compounds but the diffraction intensity is weak. The calcined product is shaped into a desired shape at a pressure of 100–500 MPa and the shaped body is fired at 1000–1200° C. By this treatment, the metal oxides product is imparted with good thermal resistance. This product is pulverized into powder for use in the oxidative coupling of methane.

If desired, the metal oxides of the above formula may be supported on a suitable inorganic carrier such as silica, alumina, titania or magnesia. By this, the surface area of the metal oxides to be contacted with methane may be improved. The support on the carrier may be effected by any conventional method such as impregnation or kneading. The sol obtained by the above-described treatment in the rotary evaporator may be advantageously used for the formation of such composite materials.

The conversion of methane into $C_2$ or higher hydrocarbons is carried out by contacting a feed gas containing methane with the metal oxides of the above formula at a temperature of 500–1000° C., preferably 500–850° C. The feed gas may contain an inert gas but the concentration of methane in the feed gas is desired to be high. The presence of molecular oxygen in the feed gas is undesirable because the selectivity is lowered. The reaction pressure is not specifically limited and may be suitably selected according to the type of the reaction bed used. The contact of methane-containing gas with the metal oxides may be effected in a fluidized bed or fixed bed system.

The metal oxides catalyst becomes gradually inactivated during repeated use. In such a case, the catalyst may be regenerated by contact with an oxygen-containing gas such as air. The regeneration is preferably performed at a temperature not lower than the temperature at which the oxidative coupling has been performed. The regenerated metal oxides catalyst may be reused for the conversion of methane.

The production of $C_2$ or higher hydrocarbons may be continously performed by simultaneously carrying out the oxidative coupling step and the regeneration step in two different zones. When a fluidized bed system is employed for each of the two steps, the continuous operation may be effected by recirculating the metal oxides catalyst between the two zones. When a fixed bed system is employed, the methane gas feed and oxygen-containing gas feed to respective zones are alternately switched to effect the continuous operation.

The following examples will further illustrate the present invention.

EXAMPLE 1

Preparation of Metal Oxides

An aqueous solution containing 0.06 mol of barium nitrate, 0.048 mol of cobalt nitrate and 0.012 mol of ferric nitrate was mixed with 0.12 mol of citric acid and 50 ml of ethylene glycol and the mixture was heated in a rotary evaporator at 100° C. under vacuo until the generation of nitrogen oxide caused by decomposition of the nitrates was ceased. The resulting mixture in the form of a sol was heated at 200° C. in an electric oven to dryness and the dried mass was further heated at 500° C. for 5 hours to completely remove organic contents. This was then pulverized and calcined at 850° C. for 10 hours. The resulting powder (2 g) was shaped into a disc under a pressure of 200 MPa and the disc was fired at 1100° C. for 10 hours. The resulting disc was pulverized for use in oxidative coupling of methane. The pulverized product (Oxide I) had the following composition:

$BaCo_{0.8}Fe_{0.2}O_y$ wherein y is in the range of 2.8–3.0.

Oxidative Coupling

Oxide I obtained above was filled in a quartz reaction tube (inside volume: 15 ml) and heated to 550° C. while feeding air. The feed of air was stopped and the air in the tube was replaced with helium gas. Then, methane gas was fed to the tube at a rate of 25 ml per minute. The discharged gases from the tube after 3 and 10 minutes from the start of the feed of methane were analyzed by gas chromatography, from the results of which the production rate (μmol per minute), yield and selectivity of ethane ($C_2$) and ethylene ($C_2$), the ratio of ethylene/ethane ($C_2/C_2$), the production rate (μmol per minute) and selectivity S of propane ($C_3$) and propylene ($C'_3$) and the production rate (umol per minute) of carbon monoxide and carbon dioxide ($CO_z$) were calculated. The yield and selectivity were calculated on carbon basis. The results are summarized in Table 1.

EXAMPLES 2–6

Using Oxide I obtained in Example 1, the oxidative coupling was performed in the same manner as described in Example 1 except that the reaction temperatures were varied as indicated in Table 1. The results are also shown in Table 1.

EXAMPLES 7–11

The preparation of metal oxides was repeated in the same manner as described in Example 1 except that 0.048 mol of strontium nitrate was used in place of 0.06 mol of barium nitrate, thereby obtaining Oxide II having the following composition:

$SrCo_{0.8}Fe_{0.2}O_y$ wherein y is in the range of 2.9–3.0.

Using Oxide II, the oxidative coupling was performed in the same manner as in Examples 1–5. The results are shown in Table 2.

EXAMPLES 12 and 13

The preparation of metal oxides was repeated in the same manner as described in Example 1 except that 0.048 mol of calcium nitrate was used in place of 0.06 mol of barium nitrate, thereby obtaining Oxide III having the following composition:

$CaCo_{0.8}Fe_{0.2}O_y$ wherein y is in the range of 2.9–3.0.

Using Oxide III, the oxidative coupling was performed in the same manner as in Examples 4 and 5. The results are shown in Table 3.

COMPARATIVE EXAMPLE 1

The preparation of metal oxides was repeated in the same manner as described in Example 1 except that no barium nitrate was used. Using the resulting oxide of Co and Fe, the oxidative coupling was performed in the same manner as in Example 1 at a temperature of 700° C. The results after 3 minutes from the commencement of the reaction are shown in Table 3.

EXAMPLE 14

Using Oxide I obtained in Example 1, the oxidative coupling was performed in the same manner as in Example 5 for 15 minutes (1st Reaction). Then, the feed of methane was replaced by the feed of air. This regeneration step was performed at 750° C. for 15 minutes. After the air in the reaction tube was replaced with helium gas, the oxidative coupling was again carried out in the same manner as above (2nd Reaction). The above regeneration and coupling procedure was repeated 3 more times. The results of the reaction after 5 and 15 minutes from the commencement of respective reactions are summarized in Table 4.

EXAMPLE 15

Example 14 was repeated in the same manner as described except that the oxidative coupling in each reaction was performed at 800° C. The regeneration was also performed at 800° C. The results are shown in Table 5.

EXAMPLES 16-18

Example 1 was repeated in the same manner as described except that the amounts of cobalt nitrate and ferric nitrate were changed to 0.036 mol and 0.024 mol, respectively to obtain metal oxides (Oxide IV) having the following composition:

$$BaCo_{0.6}Fe_{0.4}O_y$$

wherein y is in the range of 2.7-3.0.

Using Oxide IV, the oxidative coupling was performed in the same manner as Example 1 at temperatures of 700° C., 750° C. and 800° C. The results of the reaction after 5 and 15 minutes from the commencement of the reactions are summarized in Table 6.

EXAMPLE 19

Example 18 was repeated in the same manner as described except that the amount of Oxide IV was doubled. The results are also shown in Table 7.

EXAMPLE 20-22

Example 1 was repeated in the same manner as described except that the strontium nitrate was used in place of barium nitrate and that the amounts of cobalt nitrate and ferric nitrate were changed to 0.036 mol and 0.024 mol, respectively to obtain metal oxides (Oxide V) having the following composition:

$$SrCo_{0.6}Fe_{0.4}O_y$$

wherein y is in the range of 2.9-3.0.

Using Oxide V, the oxidative coupling was performed in the same manner as Example 1 except that the reaction temperature was increased to 650° C., 700° C. and 750° C. and that the amount of the metal oxide was doubled. The results of the reaction after 5 and 15 minutes from the commencement of the reactions are summarized in Table 8.

TABLE 1

| Example | Condition Temperature (°C.) | Time (min) | Ethane → Ethylene Production Rate (μmol/min) | Yield (%) | Selectivity (%) | $C'_2/C_2$ Ratio | Propane + Propylene Production (μmol/min) | Selectivity (%) | $CO_2$ Production Rate (μmol/min) |
|---|---|---|---|---|---|---|---|---|---|
| 1 | 550 | 3 | 0.25 | 0.05 | 8.1 | 0 | 0 | 0 | 5.65 |
|   | 550 | 10 | 0.18 | 0.03 | 15.5 | 0 | 0 | 0 | 1.97 |
| 2 | 600 | 3 | 1.07 | 0.2 | 50.7 | 0 | 0 | 0 | 2.08 |
|   | 600 | 10 | 1.06 | 0.2 | 82.1 | 0 | 0 | 0 | 0.46 |
| 3 | 650 | 3 | 5.07 | 1.0 | 89.0 | 0.12 | 0 | 0 | 1.25 |
|   | 650 | 10 | 3.90 | 0.7 | 94.5 | 0.12 | 0 | 0 | 0.45 |
| 4 | 700 | 3 | 13.21 | 2.5 | 91.3 | 0.33 | 0.17 | 1.8 | 2.01 |
|   | 700 | 10 | 10.40 | 2.0 | 93.4 | 0.32 | 0.18 | 2.4 | 0.93 |
| 5 | 750 | 3 | 27.70 | 5.3 | 91.9 | 0.72 | 0.77 | 3.8 | 2.56 |
|   | 750 | 10 | 18.98 | 3.6 | 92.9 | 0.71 | 0.42 | 3.1 | 1.66 |
| 6 | 800 | 3 | 30.80 | 5.8 | 93.1 | 1.00 | 0.97 | 4.4 | 1.62 |
|   | 800 | 10 | 18.72 | 3.6 | 95.1 | 1.01 | 0.45 | 3.4 | 0.59 |

TABLE 2

| Example | Condition Temperature (°C.) | Time (min) | Ethane → Ethylene Production Rate (μmol/min) | Yield (%) | Selectivity (%) | $C'_2/C_2$ Ratio | Propane + Propylene Production (μmol/min) | Selectivity (%) | $CO_2$ Production Rate (μmol/min) |
|---|---|---|---|---|---|---|---|---|---|
| 7 | 550 | 3 | 0.50 | 0.09 | 42.9 | 0 | 0 | 0 | 1.33 |
|   | 550 | 10 | 0.49 | 0.09 | 58.7 | 0 | 0 | 0 | 0.69 |
| 8 | 600 | 3 | 2.64 | 0.50 | 50.0 | 0.09 | 0 | 0 | 5.27 |
|   | 600 | 10 | 3.18 | 0.60 | 66.7 | 0.08 | 0 | 0 | 3.18 |
| 9 | 650 | 3 | 10.34 | 2.0 | 64.9 | 0.28 | 0.28 | 2.6 | 10.36 |
|   | 650 | 10 | 7.97 | 1.5 | 74.9 | 0.28 | 0.12 | 1.7 | 4.99 |
| 10 | 700 | 3 | 19.58 | 3.7 | 75.7 | 0.61 | 0.65 | 3.8 | 10.61 |
|    | 700 | 10 | 15.00 | 2.8 | 94.3 | 0.62 | 0.37 | 3.5 | 0.72 |
| 11 | 750 | 3 | 23.13 | 4.4 | 93.9 | 0.67 | 0.60 | 3.7 | 1.23 |
|    | 750 | 10 | 7.39 | 1.4 | 96.8 | 0.68 | 0.09 | 1.8 | 0.22 |

TABLE 3

| Example | Condition Temperature (°C.) | Time (min) | Ethane + Ethylene Production Rate (μmol/min) | Yield (%) | Selectivity (%) | $C'_2/C_2$ Ratio | $CO_2$ Production Rate (μmol/min) |
|---|---|---|---|---|---|---|---|
| 12 | 700 | 3 | 24.12 | 4.6 | 21.0 | 0.65 | 181.15 |
|    | 700 | 10 | 13.70 | 2.6 | 23.6 | 0.66 | 88.74 |
| 13 | 750 | 3 | 28.67 | 5.4 | 20.2 | 0.87 | 227.20 |
|    | 750 | 10 | 1.85 | 0.35 | 7.1 | 0.85 | 48.15 |
| Comp. 1 | 700 | 3 | 0 | 0 | 0 | 0 | 480.33 |

TABLE 4
(Example 14)

| Reaction Number | Condition Temperature (°C) | Time (min) | Ethane + Ethylene Production Rate (μmol/min) | Yield (%) | Selectivity (%) | $C'_2/C_2$ Ratio | Propane + Propylene Production (μmol/min) | Selectivity (%) |
|---|---|---|---|---|---|---|---|---|
| 1st | 750 | 5 | 23.6 | 4.5 | 96.1 | 0.56 | 0.49 | 3.0 |
|  | 750 | 15 | 9.4 | 1.8 | 100 | 0.55 | 0 | 0 |
| 2nd | 750 | 5 | 25.7 | 4.9 | 96.6 | 0.54 | 0.51 | 2.9 |
|  | 750 | 15 | 8.1 | 1.5 | 100 | 0.55 | 0 | 0 |
| 3rd | 750 | 5 | 25.1 | 4.8 | 96.1 | 0.59 | 0.53 | 3.0 |
|  | 750 | 15 | 10.3 | 2.0 | 99.0 | 0.60 | 0.07 | 1.0 |
| 4th | 750 | 5 | 26.2 | 5.0 | 90.5 | 0.64 | 0.73 | 3.8 |
|  | 750 | 15 | 13.8 | 2.6 | 96.5 | 0.62 | 0.20 | 2.1 |

TABLE 5
(Example 15)

| Reaction Number | Condition Temperature (°C) | Time (min) | Ethane + Ethylene Production Rate (μmol/min) | Yield (%) | Selectivity (%) | $C'_2/C_2$ Ratio | Propane + Propylene Production (μmol/min) | Selectivity (%) |
|---|---|---|---|---|---|---|---|---|
| 1st | 800 | 5 | 34.1 | 6.5 | 92.8 | 1.13 | 1.17 | 4.8 |
|  | 800 | 15 | 6.2 | 1.2 | 94.2 | 1.10 | 0.11 | 2.5 |
| 2nd | 800 | 5 | 35.9 | 6.8 | 93.6 | 0.96 | 1.08 | 4.2 |
|  | 800 | 15 | 5.5 | 1.0 | 95.1 | 1.00 | 0.09 | 2.3 |
| 3rd | 800 | 5 | 42.6 | 8.1 | 90.0 | 1.00 | 1.64 | 5.2 |
|  | 800 | 15 | 6.4 | 1.2 | 95.1 | 1.10 | 0.11 | 2.5 |
| 4th | 800 | 5 | 36.1 | 6.8 | 91.5 | 1.08 | 1.28 | 4.9 |
|  | 800 | 15 | 6.3 | 1.3 | 94.3 | 0.99 | 0.11 | 2.3 |

TABLE 6

| Example | Condition Temperature (°C) | Time (min) | Ethane + Ethylene Production Rate (μmol/min) | Yield (%) | Selectivity (%) | $C'_2/C_2$ Ratio | Propane + Propylene Production (μmol/min) | Selectivity (%) | $CO_2$ Production Rate (μmol/min) |
|---|---|---|---|---|---|---|---|---|---|
| 16 | 700 | 5 | 17.73 | 3.4 | 87.7 | 0.46 | 0.45 | 3.3 | 3.64 |
|  | 700 | 15 | 8.01 | 1.5 | 95.9 | 0.48 | 0.06 | 1.0 | 1.80 |
| 17 | 750 | 5 | 25.37 | 4.8 | 84.9 | 0.87 | 0.86 | 4.3 | 6.42 |
|  | 750 | 15 | 11.58 | 2.2 | 88.3 | 0.86 | 0.17 | 1.9 | 2.56 |
| 18 | 800 | 5 | 37.76 | 7.2 | 85.3 | 1.63 | 1.79 | 6.1 | 7.64 |
|  | 800 | 15 | 6.34 | 1.2 | 91.2 | 1.62 | 0.16 | 3.5 | 0.75 |

TABLE 7
(Example 19)

| Condition Temperature (°C) | Time (min) | Ethane + Ethylene Production Rate (μmol/min) | Yield (%) | Selectivity (%) | $C'_2/C_2$ Ratio | Propane + Propylene Production Rate (μmol/min) | Selectivity (%) | Butadiene Production Rate (μmol/min) | Selectivity (%) | $CO_2$ Production Rate (μmol/min) |
|---|---|---|---|---|---|---|---|---|---|---|
| 800 | 5 | 49.02 | 9.3 | 78.4 | 1.77 | 2.68 | 6.4 | 0.59 | 1.9 | 20.30 |
| 800 | 15 | 16.67 | 3.2 | 88.6 | 1.76 | 0.60 | 4.8 | 0 | 0 | 2.48 |

TABLE 8

| Example | Condition Temperature (°C) | Time (min) | Ethane + Ethylene Production Rate (μmol/min) | Yield (%) | Selectivity (%) | $C'_2/C_2$ Ratio | Propane + Propylene Production Rate (μmol/min) | Selectivity (%) | $CO_2$ Production Rate (μmol/min) |
|---|---|---|---|---|---|---|---|---|---|
| 20 | 650 | 5 | 8.71 | 1.7 | 37.5 | 0.25 | 0.15 | 1.0 | 3.64 |
|  | 650 | 15 | 4.57 | 0.9 | 54.4 | 0.23 | 0 | 0 | 1.80 |
| 21 | 700 | 5 | 17.35 | 3.3 | 46.0 | 0.55 | 0.55 | 2.2 | 39.04 |
|  | 700 | 15 | 10.93 | 2.1 | 58.2 | 0.56 | 0.21 | 1.7 | 15.68 |
| 22 | 750 | 5 | 31.76 | 6.0 | 47.0 | 1.22 | 1.28 | 2.8 | 67.68 |
|  | 750 | 15 | 18.86 | 3.6 | 86.8 | 1.20 | 0.55 | 3.8 | 4.10 |

What is claimed is:

1. A process for the production of hydrocarbons having 2 or more carbon atoms, comprising contacting a feed gas containing methane with an oxide of metals consisting essentially of a perovskite structure of the following formula:

$$MCo_{1-x}Fe_xO_y$$

wherein M stands for at least one of Sr and Ba, x is a number greater than 0 but not greater than 1 and y is a number in the range of 2.5–3.5, at a temperature of 500–1000° C.

2. A process as claimed in claim 1, wherein said feed gas is substantially free of oxygen gas.

3. A process as claimed in claim 1, wherein x is pb 0.1–0.6 and y is 2.7–3.1.

4. A process for the production of hydrocarbons having 2 or more carbon atoms, comprising the steps of:
  (a) introducing a feed gas containing methane into a reaction zone and contacting same with an oxide of metals contained in said reaction zone at a first temperature in the range of 500–1000° C., said oxide of metals consisting essentially of a perovskite structure of the following formula:

$$MCo_{1-x}Fe_xO_y$$

wherein M stands for at least one of Sr and Ba, x is a number greater than 0 but not greater than 1 and y is a number in the range of 2.5–3.5; and
  (b) introducing a regeneration gas containing molecular oxygen into said reaction zone and contacting same with said oxide of metals at a second temperature which is not lower than said first temperature, wherein steps (a) and (b) are alternatively repeated.

* * * * *

UNITED STATES PATENT AND TRADEMARK OFFICE
CERTIFICATE OF CORRECTION

PATENT NO. : 5,126,499
DATED : June 30, 1992
INVENTOR(S) : HAYAKAWA et al

It is certified that error appears in the above-identified patent and that said Letters Patent is hereby corrected as shown below:

Col. 9, line 7, delete "pb".

Col. 10, line 13, delete "alternatively" and insert

--alternately--.

Signed and Sealed this

Nineteenth Day of October, 1993

Attest:

BRUCE LEHMAN

Attesting Officer    Commissioner of Patents and Trademarks